United States Patent [19]

Kawashita et al.

[11] Patent Number: 4,771,129
[45] Date of Patent: Sep. 13, 1988

[54] MONOAZO DYESTUFFS CONTAINING SUBSTITUTED AMINO TRIAZINE

[75] Inventors: Hideo Kawashita, Ibaraki; Mitsuhiro Ota, Toyonaka, both of Japan

[73] Assignees: Taoka Chemical Company, Limited; Sumitomo Chemical Company, Limited, both of Osaka, Japan

[21] Appl. No.: 839,153

[22] Filed: Mar. 13, 1986

[30] Foreign Application Priority Data

Mar. 14, 1985 [JP] Japan .................................. 60-51408
Sep. 9, 1985 [JP] Japan ............................... 60-200382

[51] Int. Cl.⁴ ...................... C09B 29/34; C09B 29/36; C09B 43/16; C09D 11/02

[52] U.S. Cl. ...................... 534/803; 106/22; 534/573; 534/582; 534/583; 534/598; 534/617; 346/75

[58] Field of Search ................... 534/803, 573 L, 617

[56] References Cited

U.S. PATENT DOCUMENTS

| | | | |
|---|---|---|---|
| 1,667,312 | 4/1928 | Fritzsche et al. | 534/803 X |
| 2,643,996 | 6/1953 | Widmer et al. | 534/803 |
| 3,110,710 | 11/1963 | Rattee et al. | 534/803 |
| 3,326,887 | 6/1967 | Riat et al. | 534/803 X |
| 3,459,729 | 8/1969 | Crotti et al. | 534/803 X |
| 3,843,624 | 10/1974 | Seiler et al. | 534/573 L X |

FOREIGN PATENT DOCUMENTS

| | | | |
|---|---|---|---|
| 2062163 | 6/1971 | Fed. Rep. of Germany | 534/803 |
| 2386589 | 3/1978 | France | 534/803 |
| 38-6287 | 2/1963 | Japan | 534/803 |
| 60-188408 | 9/1985 | Japan | 534/803 |
| 61-2773 | 1/1986 | Japan | 534/803 |
| 61-2774 | 1/1986 | Japan | 534/803 |

*Primary Examiner*—Floyd D. Higel
*Attorney, Agent, or Firm*—Wegner & Bretschneider

[57] ABSTRACT

An azo compound of the formula:

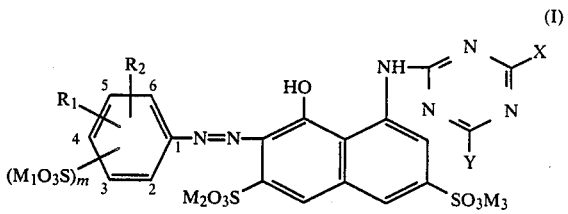

(I)

wherein $M_1$, $M_2$ and $M_3$ are, the same or different, each a hydrogen atom, an alkali metal atom, an ammonium group or an organic ammonium group; $R_1$ and $R_2$ are, the same or different, each a $C_1$–$C_3$ alkyl group, a $C_1$–$C_3$ alkoxy group, a halogen atom or a hydrogen atom; m is 1 or 2; and X and Y are, the same or different, each a $C_6$–$C_{18}$ alkylamine, alkoxyalkylamine, arylamine, aralkylamine, alkanolamine or alkarylamine residue, which is useful as a magenta color dyestuff for an aqueous ink composition, particularly for ink jet recording.

11 Claims, No Drawings

MONOAZO DYESTUFFS CONTAINING SUBSTITUTED AMINO TRIAZINE

FIELD OF THE INVENTION

The present invention relates to an azo compound and an aqueous ink composition comprising the same suitable for printing, writing, recording, stamping, etc. More particularly, it relates to an aqueous ink composition for ink jet recording, which can provide an excellent water-resistant magenta image without causing any clogging in an nozzle even when used intermittently over a long period of time.

BACKGROUND OF THE INVENTION

In general, conventional aqueous ink compositions basically comprises a dyestuff, a polyhydric alcohol or its corresponding ether as a wetting agent and water. In order to achieve good ink jet recording, these conventional ink compositions are required to have various properties. They should have appropriate values in viscosity, surface tension, specific electric conductivity, density and the like so as to adequately form droplets and control jetting directions of the droplets. Further, they should not form any precipitation during storage, in use or at rest over a long period of time. Furthermore, they should not suffer from any significant variation in the physical properties.

An outlet of a nozzle for a recording device has, in general, a diameter of 10 to 60 microns, and any precipitation within the nozzle disturbs injection of the aqueous droplets of ink from the nozzle. Even if the nozzle is not completely clogged, it is likely to produce solid or viscous material around the outlet of the nozzle, which leads to the depression of the physical property of the ink composition so designed that it falls within a desired range, whereby deterioration of the recording ability as well as the stability or response in jetting will be caused. Still, the printed image as recorded must have not only sufficiently high contrast and clarity but also water resistance, light resistance and the like.

As a magenta dyestuff for the aqueous ink composition, conventionally employed are water soluble direct dyes and acid dyes. Examples of such magenta dyestuff are C.I. Direct Red 1, 11, 37, 62, 75, 83, 99, 220 and 227 and C.I. Acid Red 87, 92, 94, 115, 131, 154, 186, and 254 (cf. Japanese Patent Kokai Publication (unexamined) Nos. 5772/1982, 141257/1983, 141262/1983, 222163/1983, 222165/1983 and 78273/1984).

Since the conventional direct dyes have, however, disadvantages such that they have low solubility in water, sufficient image concentration and contrast are not expected to a satisfactory degree, and they agglomerate and precipitate during storage or in use over a long period of time and are apt to produce the clogging in the nozzle. In addition, they produce a printed image with insufficient water resistance and only a few of them have a clear color tone. To overcome these drawbacks as seen in the conventional magenta dyestuffs, it has been proposed to incorporate in the aqueous composition and additive such as an organic amine or a surfactant as a solubilizer. However, such additive corrodes various parts of the recording device and may invite cloggings in the nozzle due to bubbling of ink composition, whereby the printed image is not sufficiently clear.

On the other hand, the use of the conventional acid dyes may enhance the color tone but produces only an printed image with insufficient qualities, particularly poor water resistance. Therefore, it is necessary to use a special paper for recording as in the case of the direct dyes.

SUMMARY OF THE INVENTION

One object of the present invention is to provide a novel azo compound which is useful as a magenta dyestuff suitable for use in an aqueous ink composition, particularly for ink jet recording.

Another object of the present invention is to provide an aqueous ink composition comprising a magenta dyestuff which has good storage stability and causes no clogging of nozzle or an ink jet recording device because of proper solubility of the dyestuff in water.

Further object of the present invention is to provide an aqueous ink composition comprising a magenta dyestuff which provides an excellent magenta image having water and light resistances.

These and other objects are accomplished by an azo compound of the formula:

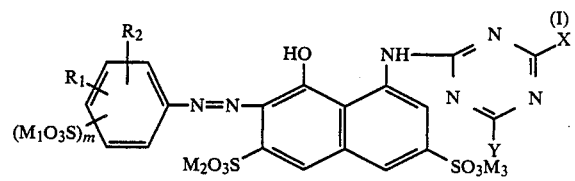

wherein $M_1$, $M_2$ and $M_3$ are, the same or different, each a hydrogen atom, an alkali metal atom, an ammonium group or an organic ammonium group; $R_1$ and $R_2$ are, the same or different, each a $C_1$–$C_3$ alkyl group, a $C_1$–$C_3$ alkoxy group, a halogen atom or a hydrogen atom; m is 1 or 2; and X and Y are, the same or different, each a $C_6$–$C_{18}$ alkylamine, alkoxyalkylamine, arylamine, aralkylamine, alkanolamine or alkarylamine residue and an aqueous ink composition comprising the azo compound (I), a wetting agent and water.

DETAILED DESCRIPTION OF THE INVENTION

Specific examples of an alkylamine, an alkoxyalkylamine, an arylamine, an aralkylamine, an alkanolamine and an alkarylamine each having 6 to 18 carbon atoms corresponding to the residues X and Y are hexylamine, 2-ethylbutylamine, diisopropylamine, heptylamine, octylamine, N,N-dibutylamine, N-ethyl-N-hexylamine, 2-ethylhexylamine, nonylamine, diamylamine, dodecylamine, dioctylamine, cetylamine, stearylamine, methoxyhexylamine, propoxybutylamine, butoxyhexylamine, hexyloxyethylamine, isobutoxypropylamine, n-butoxypropylamine, nonyloxypropylamine, lauryloxypropylamine, 2-ethylhexyloxypropylamine, aniline, aniline-sulfonic acid, toluidine, xylidine, p-ethylaniline, benzylamine, dibenzylamine, n-butylethanolamine, dodecylethanolamine, and the like.

Examples of the alkali metal atom represented by the symbols $M_1$, $M_2$ $M_3$ are sodium potassium and lithium. Examples of an organic amine corresponding to the organic ammonium group are an alkylamine, an alkoxyalkylamine, an arylamine, an aralkylamine, an alkarylamine and an alkanolamine each having not more than 18 carbon atoms including the amines as exemplified in the above.

When the residue X or Y has 5 or less carbon atoms, not only purification of such azo compound is difficult but also such compound has too large solubility in water and is inferior in affinity to the wetting agent. Therefore, it causes clogging of the nozzle, and the water resistance of the recorded image is deteriorated. When the residue X or Y has 19 or more carbon atoms, the azo compound is inferior in affinity to water and to the wetting agent so that a larger amount of the wetting agent is required to prepare the ink composition. Yet, the image density is not increased, and almost all the properties such as storage stability and an anti-nozzle clogging property are not satisfactory.

When m in the formula (I) is 0 (zero), an azo compound has poor affinity to water, while when it is 3 or larger, the water resistance of the recorded image is insufficient.

The azo compound (I) according to the present invention may be prepared, for example, by coupling anilinesulfonic acid or its salt with H-acid according to a conventional method to form a monoazo dye, and then reacting one mole of the monoazo dye, one mole of cyanuric halide and one mole of the amine corresponding to the residue X or Y in an arbitrary order.

Another method for preparing the azo compound (I) comprises coupling a diazo compound of aniline-sulfonic acid with an intermediate obtained by reacting H-acid and cyanuric halide to according to a conventional method to form a monoazo dye and then reacting the monoazo dye with the amine corresponding to the residue X or Y.

Alternatively, the cyanuric halide is reacted with H-acid and the amines corresponding to the residues X and Y in an arbitrary order and then coupling the reaction product with the diazo compound of aniline-sulfonic acid.

The condensation reaction of cyanuric halide is carried out in an aqueous medium optionally in the presence of an organic solvent at a temperature of 0° to 20° C. for the first stage condensation, a temperature of 20° to 60° C. for the second stage condensation and a temperature of 60° to 110° C. for the third stage condensation. The addition of a surfactant may increase the reaction rate. When sulfonic acid is converted to the organic ammonium salt, firstly an azo compound (I) wherein all or a part of $M_1$, $M_2$ and $M_3$ are a hydrogen atom, an alkali metal atom or an ammonium group is produced. Then, said azo compound (I) is added to an aqueous medium optionally containing an organic solvent, an organic amine is added to the mixture and its pH is adjusted to 4 to 5 by the addition of an inorganic or organic acid to form a desired organic ammonium salt.

The wetting agent may be a conventionally used one for an aqueous ink composition. Examples of such wetting agent are polyhydric alcohols, cellosolves, carbitols, and the like. Specifically, there are exemplified ethylene glycol, diethylene glycol, triethylene glycol, propylene glycol, glycerol, polyethylene glycol, ethylene glycol monoethyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether and the like. In addition, any solubilizer for dyestuff as conventionally employed may be used. Examples of the solubilizer are dimethylformamide, pyrolidone, alcohols, alkanolamines, and the like.

In the ink composition of the invention, the amount of the azo compound (I) is usually from 0.5 to 20 parts by weight, preferably from 1 to 15 parts by weight per 100 parts by weight of the whole ink composition.

Usually, the azo compound (I) develops magenta, and may be used alone or in combination. In addition, any dyestuff used in a conventional aqueous ink composition may be incorporated in the ink composition of the invention in such amount that the characteristic properties of the azo compound (I) are not deteriorated.

The wetting agent is used in an appropriate amount so as to impart the characteristic properties desired for a recording vehicle of the ink composition. Its amount may be preferably from 10 to 80 parts by weight per 100 parts by weight of the ink composition. Usually, one kind of the wetting agent is used, although two or more kinds of them may be used insofar as they do not adversely affect each other.

In order to provide the ink composition of the invention with additional characteristic properties, at least one of other conventional additives may be incorporated in the composition. Specific examples of such additives are antiseptics or fungicides (.e.g sodium dehydroacetate, 2,2-dimethyl-6-acetoxydioxane, ammonium thioglycollate, etc.), rust preventives (e.g. acid sulfites, sodium thiosulfate, dicyclohexylammonium nitrite, etc.), UV light absorbers, viscosity regulators, surfactants, pH adjusters, specific resistance adjusters, IR light absorbers and the like.

Unlike the conventional magenta dyestuffs, the azo compound (I) of the invention is characteristic in that, on one hand, it has comparatively poor solubility in water and, on the other hand, it has improved affinity to polyhydric alcohols, cellosolves and carbitols. Therefore, it can be used in a variety of aqueous ink compositions and preserve a solution state with a high stability against the variation of the composition caused during the storage and/or the use. In addition, the azo compound (I) is easily isolated with high purity from the by-product inorganic materials so that the image recorded by the azo compound (I) has high density and clarity.

The aqueous ink composition of the invention is suitable for printing, writing, recording, stamping, ink jet recording, coating, and coloring a molded article and a film made of a synthetic resin.

The present invention will be hereinafter explained further in detail by following examples in which part(s) are by weight unless otherwise indicated.

EXAMPLE 1

1-Amino-8-hydroxynaphthalin-3,6-disulfonic acid (31.8 g) was dissolved in water (100 g) under a neutral condition. The aqueous solution was dropwise added to a mixture of ice-cooled water (200 g), cyanuric chloride (18.5 g) and 35% hydrochloric acid (11 g). Then, 2N sodium hydroxide was continuously added to the mixture with maintaining pH of the mixture at 1.5 till the completion of the condensation reaction.

On the other hand, to water (200 g) and 35% hydrochloric acid (22 g), orthanilic acid (16.5 g) was added and cooled to a temperature of 0° to 2° C. with ice followed by the addition of sodium nitrite (6.6 g) to proceed diazotation. The produced diazonium salt was poured into the mixture prepared in the previous step at a temperature of 0° to 5° C. Then, pH of the mixture was adjusted to 6.0 to 7.0 with sodium carbonate. After completing the coupling reaction, the mixture was subjected to salting-out and the precipitated crystalline product was collected by filtration.

A solution of the azo compound (3) in methanol had $\lambda_{max}$ at 545 nm and absorbance of 0.420 (21 mg/l).

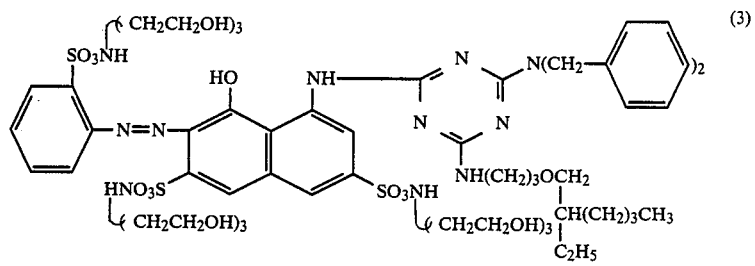
(3)

The prepared azo dye was dissolved in water (1 liter), and 2-ethylhexyloxypropylamine (19 g) was added and kept standing at 60° C., pH of 6.5 to 6.8 for 3 hours. Then, dibenzylamine (20 g) was added, and the mixture was kept standing at a temperature of 98° to 100° C., pH of 6.5 to 6.8 for 3 hours. The resulting azo compound was isolated from water and thoroughly washed with water to give the reddish brown powder (112 g) having the following chemical formula (1).

A solution of the azo compound (1) in methanol had $\lambda_{max}$ at 545 nm and absorbance of 0.531 (20 mg/l).

EXAMPLE 4

To a dispersion of orthanilic acid (16.5 g) in water (200 ml), 35% hydrochloric acid (22 g) was added and cooled to a temperature of 0° to 2° C. To the mixture, sodium nitrite (6.6 g) was added to proceed diazotation. Then, soda ash was added to adjust pH at 4.

The liquid containing the diazo compound was then added to a solution of H-acid (31.8 g) in water (100 g) pH of which was adjusted to 6.5 to 7.0 with sodium hydroxide to proceed a coupling reaction. The reaction

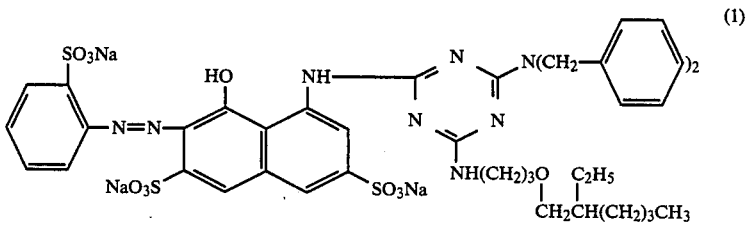
(1)

EXAMPLE 2

In the same manner as in Example 1 but using 2-ethylhexyloxypropylamine in place of dibenzylamine, the reactions were carried out to give the reddish brown powder (84 g) having following formula (2).

A solution of the azo compound (2) in methanol had $\lambda_{max}$ at 545 nm and absorbance of 0.533 (20 mg/l).

mixture was subjected to salting-out with 20% saline and filtered. The filtration cake was dispersed in water (250 ml). The mixture containing the coupling product was poured in a dispersion of cyanuric chloride (18.5 g) in water (350 ml) at a temperature not higher than 5° C. over 30 minutes. The reaction was proceeded at a temperature not higher than 5° C. for 4 hours with adjusting pH at 6.5 to 7 by the addition of soda ash. Then, to the

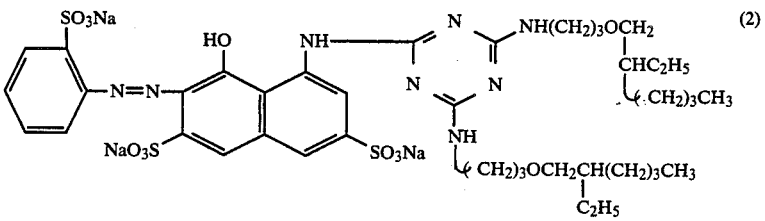
(2)

EXAMPLE 3

To a dispersion of the reddish brown powder compound (1) prepared in Example 1 (30 g) in water (500 ml) at 30° C., triethenolamine (12 g) was added and stirred for 2 hours with keeping the pH value at 4 to 5. The reaction mixture was filtered, washed with water and dried to give the reddish brown powder (39 g) having following formula (3).

reaction mixture, butoxypropylamine (12.5 g) was added and kept standing at 60° C., pH of 6.5 to 6.8 for 3 hours. Thereafter, dodecylamine (13.0 g) was added and kept standing at a temperature of 98° to 100° C., pH of 6.5 to 6.8 for 3 hours. The resulting azo compound was isolated from water, thoroughly washed with water and dried to give the reddish brown powder (95 g) having the following formula (4).

A solution of the azo compound (4) in methanol had $\lambda_{max}$ at 545 nm and absorbance of 0.566 (20 mg/l).

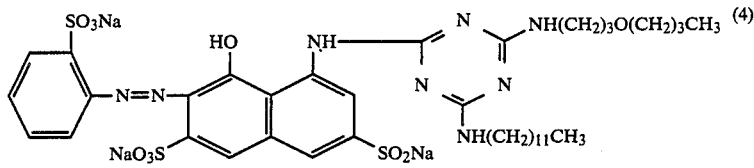

EXAMPLE 5

To a mixture of ice water (200 g), cyanuric chloride (18.5 g) and 35% hydrochloric acid (11 g), a solution of H-acid (31.8 g) in water (100 g) was added and kept at a temperature of not higher than 5° C., pH of 1.5 to 2.0 for 4 hours. To the mixture, hexylamine (21 g) was added and kept at 60° C. for 3 hours and then at a temperature of 90° to 98° C., pH of 6.0 to 7.0 for 3 hours. Then, a cooled diazonium salt corresponding orthanilic acid (16.5 g) was added to proceed a coupling reaction. The produced azo compound was isolated from water, thoroughly washed with water and dried to give the reddish brown powder (69 g) having the following formula (5).

A solution of the azo compound (5) in methanol (20 mg/l) had $\lambda_{max}$ at 545 nm and absorbance of 0.632.

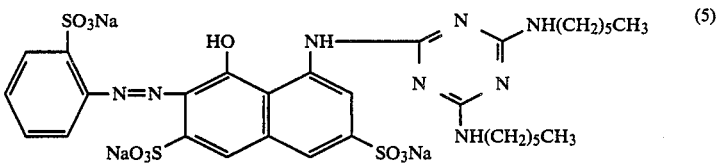

EXAMPLE 6

In the same manner as in one of Examples 1 to 5, the compounds (6) to (14) shown in Table 1 were prepared.

For comparison, dyestuffs shown in Table 2 were used.

TABLE 1

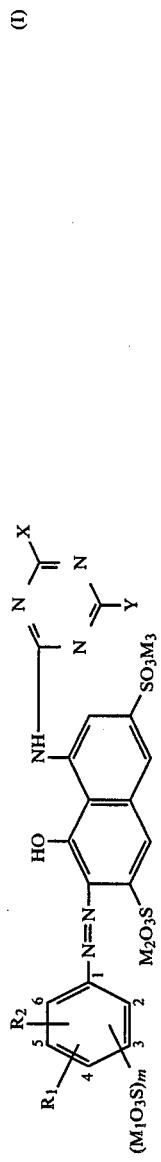
(I)

| Compound No. | (M₁O₃S)ₘ m | (M₁O₃S)ₘ position | R₁ | R₁ position | R₂ | R₂ position | M₁ | M₂ | M₃ | X | Y | $\lambda_{max}$ | Absorbance (20 mg/l) |
|---|---|---|---|---|---|---|---|---|---|---|---|---|---|
| 6 | 1 | 4 | H | | H | | Na | Na | Na | NH(CH₂)₃OCH₂—CH(C₂H₅)—CH₃(CH₂)₃ | -CH₂-N(-CH₂-C₆H₅)-CH₂-C₆H₅ | 548 | 0.531 |
| 7 | 1 | 3 | H | | H | | K | K | K | NH(CH₂)₃OCH₂—CH(C₂H₅)—CH₃(CH₂)₃ | NHCH₂-C₆H₅ | 547 | 0.554 |
| 8 | 2 | 2,4 | H | | H | | Li | Li | Li | NHC₁₈H₃₇ | NH-C₆H₄-C₂H₅ (p) | 545 | 0.510 |
| 9 | 1 | 2 | OCH₃ | 4 | H | | NH₃C₄H₉ | NH₃C₄H₉ | NH₃C₄H₉ | N(C₆H₁₃)₂ | NH-C₈H₁₇ | 552 | 0.480 |
| 10 | 1 | 2 | Cl | 5 | H | | NH₃CH₂CH₂OH | NH₃CH₂CH₂OH | NH₃CH₂CH₂OH | NH(CH₂)₃OC₁₁H₂₃ | NH-C₆H₄-SO₃Na (m) | 550 | 0.448 |

TABLE 1-continued (I) Structure: naphthalene-based azo dye with substituents (M₁O₃S)ₘ, R₁, R₂ on phenyl ring connected via N=N to naphthalene bearing OH, NH, SO₃M₂ (M₂O₃S) and triazine ring with X and Y substituents.

| Compound No. | (M₁O₃S)ₘ m | (M₁O₃S)ₘ position | R₁ position | R₁ | R₂ position | R₂ | M₁ | M₂ | M₃ | X | Y | $\lambda_{max}$ | Absorbance (20 mg/l) |
|---|---|---|---|---|---|---|---|---|---|---|---|---|---|
| 11 | 1 | 2 | 5 | CH₃ | | H | NH₃(CH₂)₃OCH₂<br>C₂H₅—CH<br>CH₃(CH₂)₃ | NH₃(CH₂)₃OCH₂<br>C₂H₅—CH<br>CH₃(CH₂)₃ | NH₃(CH₂)₃OCH₂<br>C₂H₅—CH<br>CH₃(CH₂)₃ | NH(CH₂)₃OCH₂<br>C₂H₅—CH<br>CH₃(CH₂)₃ | N(CH₂—C₆H₅)₂ | 550 | 0.359 |
| 12 | 1 | 2 | 5 | CH₃ | 4 | OC₂H₅ | NH₄ | NH₄ | NH₄ | NH(CH₂)₃OC₄H₉ | N(CH₂CH₂OH)(C₁₂H₂₅) | 553 | 0.522 |
| 13 | 1 | 2 | | H | | H | NH₃(CH₂)₃OCH₂<br>C₂H₅—CH<br>CH₃(CH₂)₃ | Na | Na | NH(CH₂)₃OCH₂<br>C₂H₅—CH<br>CH₃(CH₂)₃ | N(CH₂—C₆H₅)₂ | 545 | 0.458 |
| 14 | 1 | 2 | | H | | H | NH₃(CH₂)₃OCH₂<br>C₂H₅—CH<br>CH₃(CH₂)₃ | NH₃(CH₂)₃OCH₂<br>C₂H₅—CH<br>CH₃(CH₂)₃ | Na | NH(CH₂)₃OCH₂<br>C₂H₅—CH<br>CH₃(CH₂)₃ | N(CH₂—C₆H₅)₂ | 545 | 0.402 |

TABLE 2

| Compound No. | (M₁O₃S)ₘ m | (M₁O₃S)ₘ position | R₁ position | R₂ position | M₁ | M₂ | M₃ | X | Y |
|---|---|---|---|---|---|---|---|---|---|
| A | 1 | 2 | H | H | Na | Na | Na | NHC₂H₅ | NHC₂H₅ |
| B | 2 | 2,4 | H | H | Na | Na | Na | NHC₂H₅ | NHC₄H₉ |
| C | 1 | 4 | H | H | Na | Na | Na | NHC₂₄H₄₉ | NHC₂₄H₄₉ |

EXAMPLES 7 TO 15 AND COMPARATIVE EXAMPLES 1 TO 3

Components shown in Table 3 were thoroughly mixed. The resultant mixture was sufficiently stirred at 50° C. and filtered under pressure by means of a membrane filter (0.5 micron) to obtain an ink composition for recording, of which storage stability, jet stability, image clarity and water resistance were examined. The examinations were carried out as follows:

STORAGE STABILITY

The ink composition was sealed in a Pyrex-made test tube and allowed to stand at 0° C. or 50° C. for one month. Thereafter, degree of precipitation was observed, and evaluated according to the following criteria:

⊙ : No precipitation
○ : Scarce precipitation
△: A little precipitation
X: Much precipitation

JET STABILITY

The ink composition was charged in an ink jet recording device provided with a nozzle of 30 microns in diameter and jetted for 24 hours, during which jetting was effected with cycles each consisting of one second jetting and one second rest. After the jetting was stopped, the ink composition was allowed to stand at room temperature for 10, 20, 30, 60 or 90 days and again subjected to jetting, at which observation was made on whether clogging was produced. The jet stability was represented by the maximum number of days after which re-jetting could be carried out without clogging.

IMAGE CLARITY

The ink composition was jetted for recording by the means of the same device as used for evaluating the jet stability, and the image clarity on the recording was visually observed and evaluated according to the following criteria:

⊙ : Excellent
○ : Normal
△: Not sufficient
X: Poor

WATER RESISTANCE

An image was recorded on a sheet of wood free paper and immersed in water for one minute. Then, a degree of bleeding of the dye was visually observed and evaluated according to the following criteria:

⊙ : No bleeding
○ : Slight bleeding
△: Bleeding
X: Heavy bleeding

As understood from the results in Table 3, it is clear that the ink composition of the invention gives an enhanced magenta image, can be stably stored over a longer period of time and is improved in nozzle clogging in comparison with the conventional ink composition.

TABLE 3

| | Example No. | | | | | | | | | | | |
|---|---|---|---|---|---|---|---|---|---|---|---|---|
| | 7 | 8 | 9 | 10 | 11 | 12 | 13 | 14 | 15 | Comp. 1 | Comp. 2 | Comp. 3 |
| Azo compound No. | 1 | 2 | 14 | 10 | 4 | 3 | 11 | 5 | 13 | A | B | C |
| (parts) | 3.5 | 3.5 | 3.5 | 3.5 | 3.5 | 3.5 | 3.5 | 3.5 | 3.5 | 3.5 | 3.5 | 3.5 |
| Ethylene glycol | | 25 | 30 | 20 | | 20 | | | 25 | | 5 | 5 |
| Diethylene glycol | | | | | 10 | | 20 | | | 20 | 15 | 15 |
| Polyethylene glycol #200 | 8 | | | | 10 | 20 | 20 | 10 | 10 | 20 | 18 | 20 |
| Glycerol | 1 | | 10 | | | | | | | | | |
| Ethylcellosolve | | | | 10 | 10 | | | | | | | |
| Methyl carbitol | | | | | 10 | | | | | | | |
| Butyl carbitol | 1 | | 10 | 20 | | | 20 | 4 | | 10 | 10 | 10 |
| N—Methyl-2-pyrolidone | 24 | 5 | | | 10 | | | | 5 | | | |
| Triethenolamine | 2 | 2 | 2 | 2 | 2 | 2 | 2 | 2 | 2 | | 2 | |
| Ion exchanged water | 50.5 | 54.5 | 44.5 | 31.5 | 44.5 | 54.5 | 36.5 | 80.5 | 54.5 | 46.5 | 46.5 | 46.5 |
| Storage stability | | | | | | | | | | | | |
| At 0° C. | ⊙ | ⊙ | ⊙ | ○ | ⊙ | ⊙ | ⊙ | ⊙ | ⊙ | ○ | ○ | △ |
| At 50° C. | ⊙ | ⊙ | ⊙ | ⊙ | ⊙ | ⊙ | ⊙ | ⊙ | ⊙ | ○ | △ | △ |
| Jetting stability (days) | 90 | 90 | 90 | 90 | 90 | 90 | 90 | 90 | 90 | 20 | 30 | 20 |
| Image clarity | ⊙ | ⊙ | ⊙ | ⊙ | ○ | ⊙ | ⊙ | ⊙ | ⊙ | ⊙ | ⊙ | ○ |
| Color tone | red | red | red | red | red | red | red | red | red | red | red | red |
| Water resistance | ⊙ | ⊙ | ⊙ | ⊙ | ⊙ | ⊙ | ⊙ | ⊙ | ⊙ | △ | X | ⊙ |

What is claimed is:

1. An azo compound of the formula:

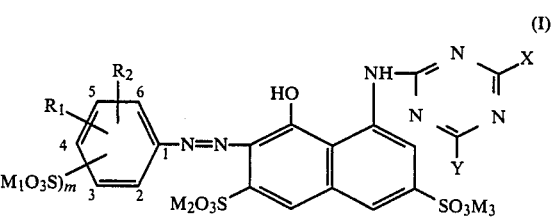

(I)

wherein M₁, M₂ and M₃ represent the same or different, hydrogen, alkali metal, ammonium or ammonium substituted with alkyl, alkoxyalkyl, aryl, aralkyl, alkaryl and alkanol each having 1 to 18 carbon atoms; $R_1$ and $R_2$ represent the same or different, $C_1$-$C_3$ alkyl, $C_1$-$C_3$ alkoxy, halogen or hydrogen, m is 1 or 2; and X and Y represent the same or different, alkylamino, alkoxyalkylamino, arylamino, aralkylamino, or alkarylamino each having 6-18 carbon atoms.

2. The azo compound according to claim 1, wherein m is 1 (one).

3. The azo compound according to claim 2, wherein the residue —$M_1O_3S$ is present at an ortho-position with respect to the azo group.

4. The azo compound according to claim 1, wherein $R_1$ and $R_2$ are both hydrogen.

5. The azo compound according to claim 1, wherein $M_1$, $M_2$ and $M_3$ are all sodium.

6. The azo compound according to claim 3, wherein $M_1$, $M_2$ and $M_3$ are all sodium.

7. The azo compound according to claim 1, wherein X and Y are both alkoxyalkylamino.

8. The azo compound according to claim 1, wherein X is alkoxyalkylamino and Y is aralkylamino.

9. The azo compound according to claim 5, wherein X is alkoxyalkylamino residue and Y is aralkylamino.

10. The azo compound according to claim 8, wherein aralkylamino is benzylamino or dibenzylamino.

11. The azo compound according to claim 8, wherein alkoxyalkylamino is 2-ethylhexyloxypropylamino.

* * * * *